: US 7,242,750 B2
(45) Date of Patent: Jul. 10, 2007

(12) United States Patent
Tsujita (54) RADIOTHERAPY APPARATUS

(75) Inventor: Kazuhiko Tsujita, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 136 days.

(21) Appl. No.: 11/034,885

(22) Filed: Jan. 14, 2005

(65) Prior Publication Data

US 2005/0185766 A1  Aug. 25, 2005

(30) Foreign Application Priority Data

Jan. 19, 2004  (JP) .............................. P2004-010393

(51) Int. Cl.
*G21K 1/02*  (2006.01)

(52) U.S. Cl. .................... 378/152; 378/65; 378/147; 378/150

(58) Field of Classification Search ................ 378/65, 378/147, 148, 149, 150, 151, 152, 153

See application file for complete search history.

(56) References Cited

U.S. PATENT DOCUMENTS 6,918,698 B2 *  7/2005  Nordmeyer et al. ........ 378/205
6,920,203 B2 *  7/2005  Short et al. .................. 378/147

FOREIGN PATENT DOCUMENTS

JP         2002-253686         9/2002

* cited by examiner

*Primary Examiner*—Edward J. Glick
*Assistant Examiner*—Chih-Cheng Glen Kao
(74) *Attorney, Agent, or Firm*—Oblon, Spivak, McClelland, Maier & Neustadt, P.C.

(57) ABSTRACT

A radiotherapy apparatus comprising a radiation source configured to radiate a radiation ray, a multi leaf collimator, including a plurality of leaves, configured to limit a radiation range of the radiation ray and a drive unit configured to move at least one of the leaves with an ultrasonic wave.

15 Claims, 9 Drawing Sheets

RADIOTHERAPY APPARATUS

CROSS-REFERENCE TO RELATED APPLICATIONS

This application is based upon and claims the benefit of priority from prior Japanese Patent Application No. 2004-10393 filed on Jan. 19, 2004, the entire contents of which are incorporated herein by reference.

FIELD OF THE INVENTION

The present invention relates generally to a radiotherapy apparatus which treats a diseased part, such at a tumor by using a radiation ray, and relates to its multi-leaf collimator limiting a range of the radiation ray.

BACKGROUND

A multi-leaf collimator of a radiotherapy apparatus includes groups of leaves, a main material of which is heavy metal, such as tungsten, and the leaves in each group are closely adjacent. Pairs of the groups of leaves are positioned in a radiation direction of a radiation ray. The groups of each pair move in close and opposite directions, mutually. A drive unit which moves each leaf in a conventional radiotherapy apparatus includes drive gears which contacts cogs formed in edges of leaves and are connected to a motor via shafts. The drive unit is described in Japanese Patent Disclosure (Kokai) No. 2002-253686, page 3 and FIG. 12, for example. Since it is required to move each leaf in the close and opposite directions according to a range of the radiation ray, namely a diseased part to be treated, a driving mechanism is provided with respect to each leaf A conventional multi-leaf collimator includes the groups, each of which has about 40 adjacent leaves with a thickness of about 3 mm. Although it is theoretically possible to approximate the radiation range to the medical treatment range by reducing thickness of the leaves and increasing number of leaves, it is actually difficult to reduce the thickness of the leaves due to the drive gears which move the leaves and the shafts which connects the drive gears and the motor. Moreover, it is also a problem that the drive unit increases in size and in weight.

Furthermore, backlash could occur in such a gear mechanism, and accuracy of move control of the leaf is reduced. Therefore, when the radiation range is set, positions of the leaves are shifted, it is difficult to accurately set the radiation range, and it could be a problem that the radiation ray is radiated to a normal part of a patient. The above mentioned Japanese Patent Disclosure (Kokai) No. 2002-253686 discloses a gear mechanism which avoids the backlash, however the gear mechanism increases in size.

SUMMARY

One object of the present invention is to ameliorate the above-mentioned problems.

According to one aspect of the present invention, there is provided a radiotherapy apparatus comprising a radiation source configured to radiate a radiation ray, a multi leaf collimator, including a plurality of leaves, configured to limit a radiation range of the radiation ray and a drive unit configured to move at least one of the leaves with an ultrasonic wave. According to another aspect of the present invention, there is provided a radiotherapy apparatus comprising a radiation source configured to radiate a radiation ray, a multi leaf collimator, including a plurality of leaves, configured to limit a radiation range of the radiation ray and means for moving at least one of the leaves with an ultrasonic wave. According to another aspect of the present invention, there is provided a method for controlling a radiotherapy apparatus comprising radiating a radiation ray, limiting a radiation range of the radiation ray with a plurality of leaves and moving at least one of the leaves with an ultrasonic wave.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF EXEMPLARY EMBODIMENTS

An embodiment of a radiotherapy apparatus is explained in detail with reference to FIGS. 1 to 9.

Figure 1:
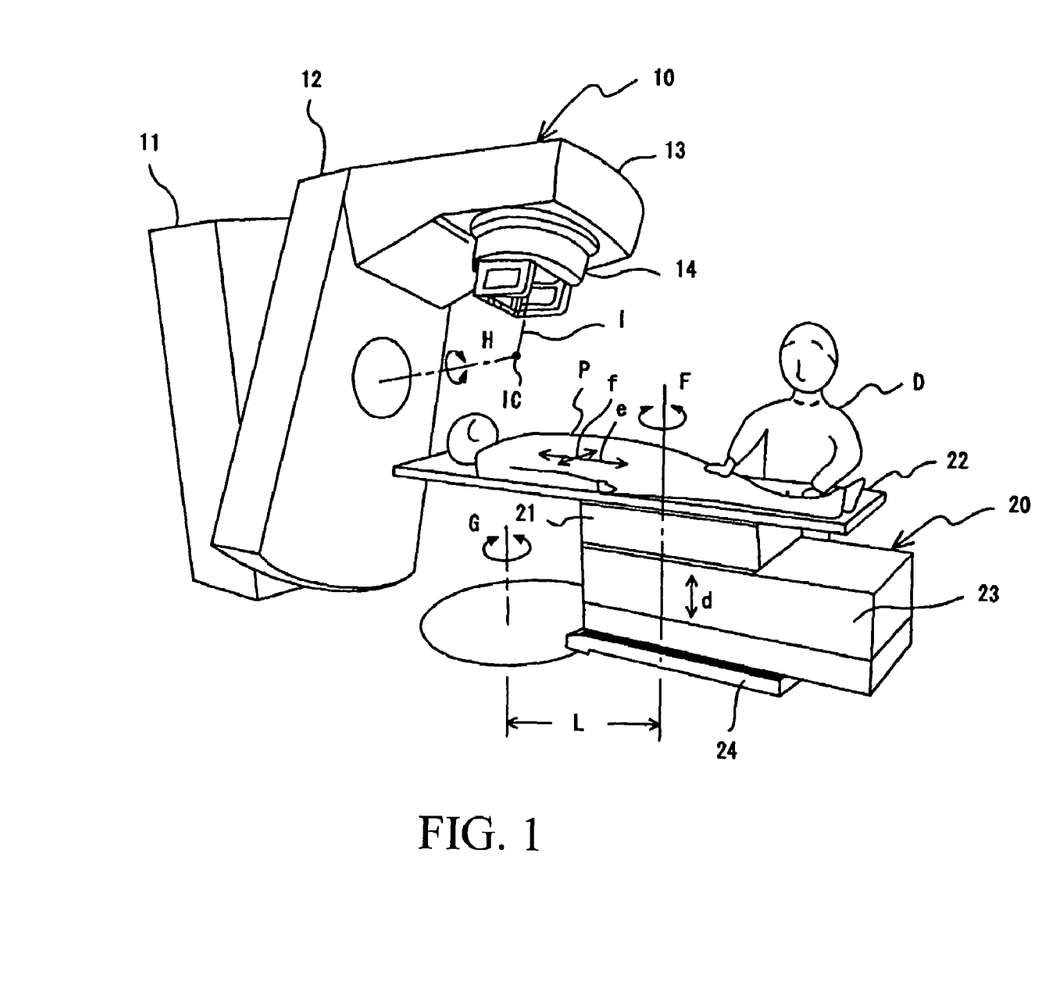
FIG. 1 is a perspective view of a radiotherapy apparatus.

The radiotherapy apparatus is mainly explained with reference to FIG. 1 which is a perspective view.

The radiotherapy apparatus includes a radiation unit 10 which radiates a radiation ray from a radiation source to a patient, and a bed unit 20 on which the patient P is laid and a position of the radiation range is set.

The radiation unit 10 includes a fixed gantry 11 which is fixed on a floor, a rotation gantry 12 which rotates and is supported by the fixed gantry 11, a radiation head 13 which is positioned on a top part of the rotation gantry 12, and a collimator 14 is included in the radiation head 13. The rotation gantry 12 can be rotated through about 360 degrees around a horizontal rotation center axis H of the fixed gantry 11, and the collimator 14 can be also rotated around radiation axis I. An intersection of the rotation center axis H and the radiation axis I is called as an isocentre IC. The rotation gantry 12 stops when a fixed radiation method is performed or rotates when several radiation methods, such as a rotation radiation method, a pendulum radiation method, or an intermittent radiation method is performed.

The bed unit 20 is positioned on the floor and rotates within a predetermined angle range in a G-arrow direction along a circular arc around the isocentre IC. A top plate 22 on which the patient is laid is supported by an upper mechanism 21 of the bed unit 20. The upper mechanism 21 moves the top plate 22 in a forward and backward direction shown as Arrow e and in a right and left direction shown as Arrow f.

The upper mechanism 21 is supported by a lift mechanism 23. The lift mechanism 23 includes a link mechanism, for example, when the link mechanism goes up and down in a direction shown as Arrow d, the upper mechanism 21 and the top plate 22 move in the up and down direction in a predetermined range. The lift mechanism 23 is supported by a lower mechanism 24. The lower mechanism 24 includes a rotation mechanism which rotates the lift mechanism 23 in a direction shown as Arrow F centering on a center at a distance L from the isocentre IC. That is, the upper mechanism 21 and the top plate 22 with the lift mechanism 23 can move in the direction shown as Arrow F in a predetermined range.

A positioning of the patient P to be treated and a setting of the radiation range of the collimator 14 are performed a staff D, such as a doctor.

When the radiation treatment is performed, it is desired that the radiation ray is radiated only to a diseased part, such as a tumor and that a normal tissue is not damaged. Therefore, in order to reduce the radiation ray radiated to the normal part, the collimator 14 which limits the radiation range is provided in the radiation head 13 as the collimator 14 can rotate around the radiation axis I.

Figure 2:
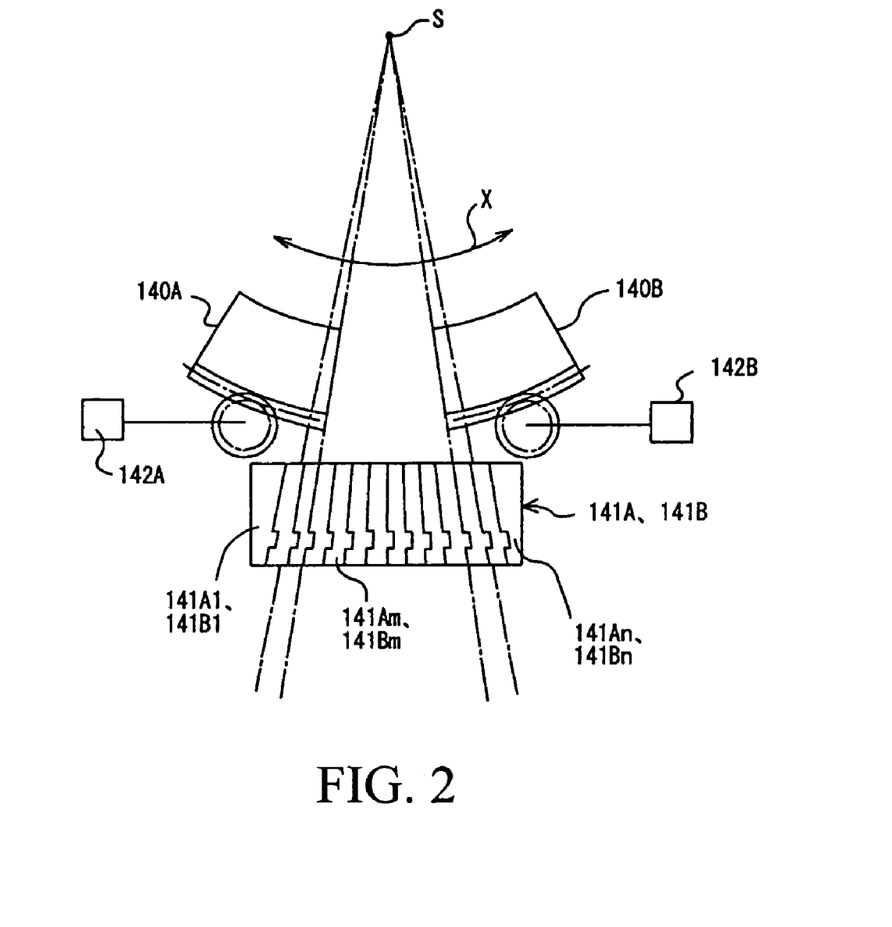
FIG. 2 is a side view of a collimator of the radiotherapy apparatus.
Figure 3:
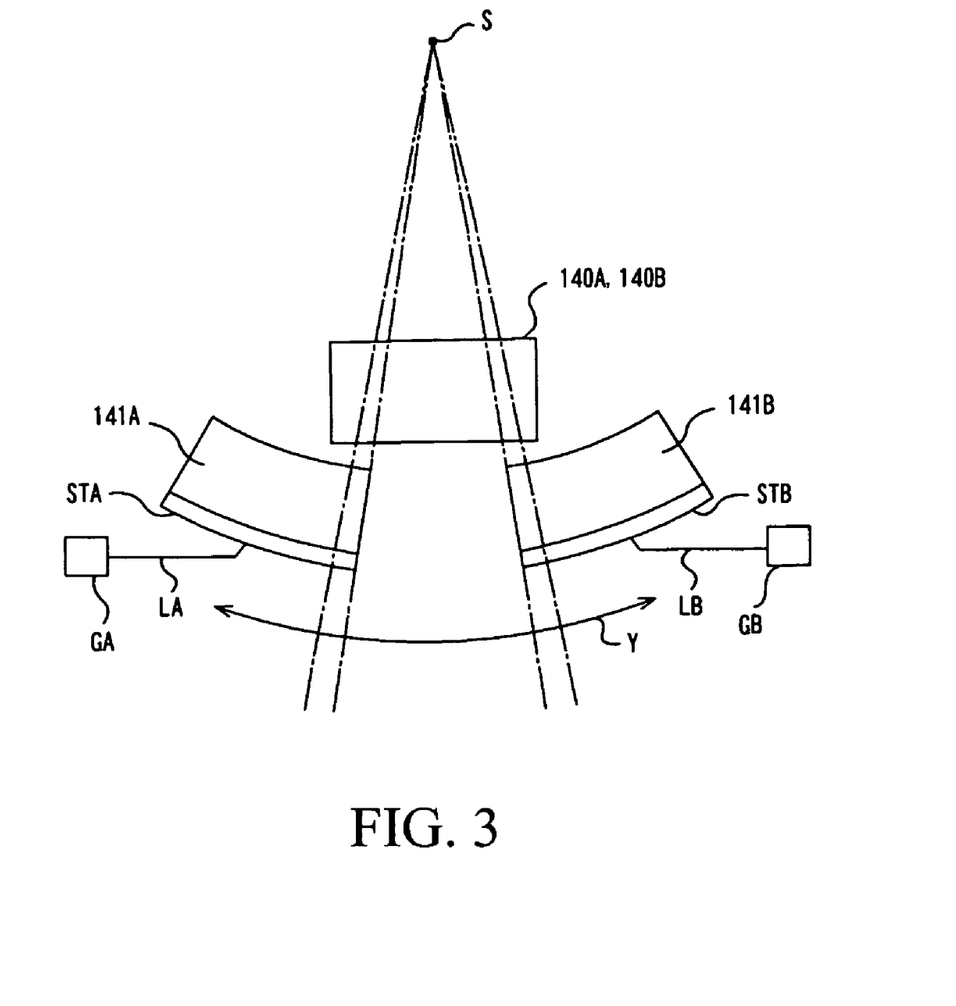
FIG. 3 is a side view perpendicular to FIG. 2.
Figure 4:
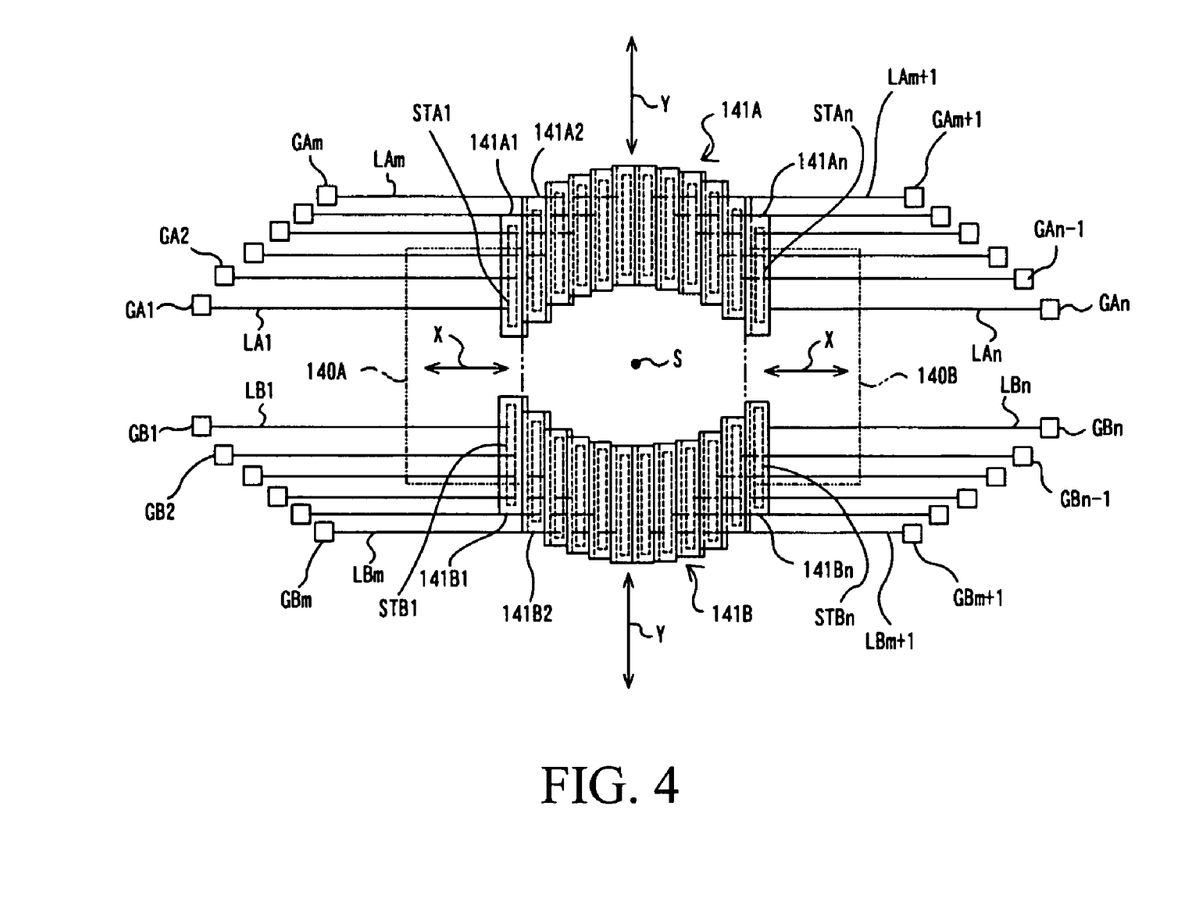
FIG. 4 is an illustration of pair of groups of the leaves in FIG. 2 and FIG. 3.

The collimator 14 is shown in FIGS. 2 to 4, and is explained in detail. FIGS. 2 and 3 are illustrations for explaining a first pair of the leaves and a second pair of groups of leaves and are perpendicular, mutually. FIG. 4 is a flat view indicating the second pair of leaves.

The collimator 14 includes the first pair 140 of leaves mainly made of heavy metal, such as tungsten, and the second pair 141 of leaves, and the first and second pairs are arranged along a radiation direction of the radiation ray radiated from a radiation source S. As shown in FIGS. 2 and 3, the pairs 140 and 141 are divided into two groups 140A and 140B, and 141A and 141B, respectively.

The first leaves 140A and 140B which are close to the radiation source S work as a single component, and move in a direction shown as Arrow X along an arc-shaped plane centering on the radiation source S. Each group is moved closer and farther, mutually, by first drive units I 42A and 1 42B which transfer mechanical powers to the leaves from the motor via the gear mechanisms.

The second groups 141A and 141B of leaves which is far from the radiation source S, as shown in FIG. 3, mutually move closer and farther, in a direction shown as Arrow Y which is along an arc-shaped plane centering on the radiation source S and which is perpendicular to the direction of the movement of the first leaves 140A and 140B. The second groups 141A and 141B of leaves, as shown in FIG. 2 and FIG. 4, includes a plurality of leaves 141A1 to 141An and 141B1 to 141Bn, and the leaves 141A1 to 141An and 141B1 to 141Bn are adjacent, respectively. The leaves 141A1 to 141An and 141B1 to 141Bn are mainly made of heavy metal.

The leaves 141A1 to l4lAn and 141B1 to l4lBn of the second groups 141A and 141B are moved in the arc-shaped plane by second drive units. The second drive units include stators STA1 to STAn and STB1 to STBn which are attached to edges of the leaves, signal lines LA1 to LAn and LB1 to LBn connected with the stators and a high-voltage generation units GA1 to GAn and GB1 to GBn which supply high-voltage to the stators via the signal lines. In this embodiment, an operation of the second drive units and 113B1 to 113Bn which move the leaves 141A1 to 141An and 141B1 to 141Bn of the second groups 141A and 141B is different from an operation of the first drive units 142A and 142B which move the first leaves 140A and 140B. Switch circuits which are connected to the second drive units select the leaf to be moved among the second groups of leaves.

Figure 5:
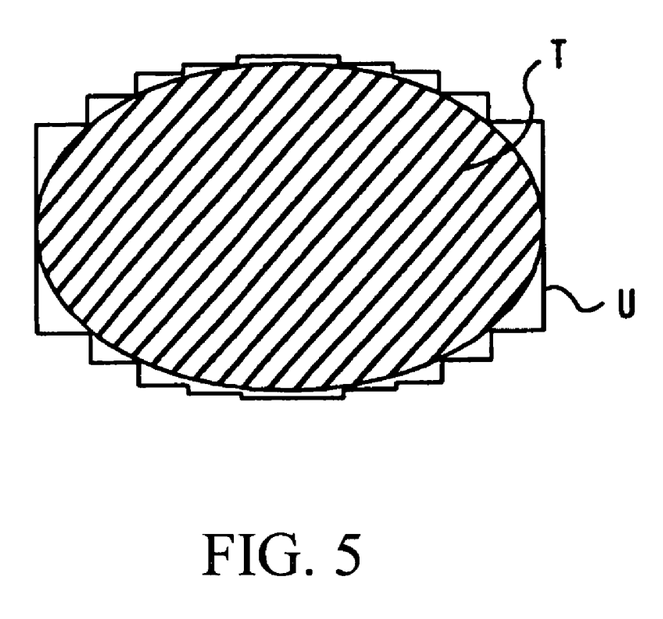
FIG. 5 is an illustration for explaining a radiation range formed by a collimator.

By a combination of the close and far movement of the first leaves 140A and 140B in the X direction and the close and far movement of the second groups of leaves 141A and 141B in the Y direction, an irregular radiation range U which is approximated to a diseased part T can be created, as shown in FIG. 5.

The second drive units which move the leaves 141A1 to 141An and 141B1 to 141Bn of the second groups 141A and 141B.

Figure 6:
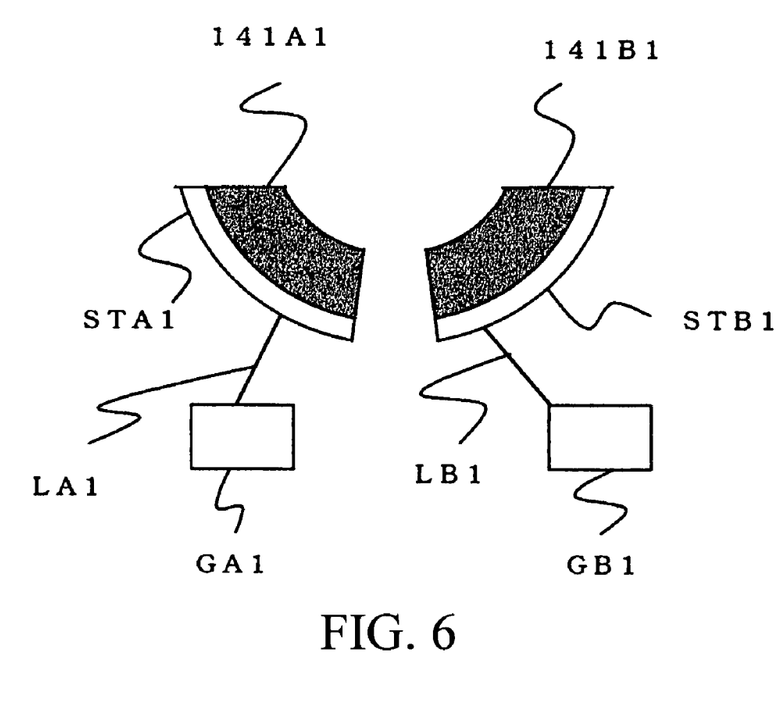
FIG. 6 is an illustration for explaining a main part of a drive unit for movement of leaves in the collimator.

FIG. 6 shows an illustration for explaining the second drive units which move the leaves 141A1 and 141B1. The edges of the leaves 141A1 and 141B1 strongly contact the stators STA1 and STB1 with contact pressure. The stators STA1 and STB1 include metal materials M, elastic bodies EL and piezoelectric transducers CE. The piezoelectric transducer CE is known as an ultrasonic transducer, such as piezoelectric ceramic, which generates ultrasound according to received high frequency electric signal. The piezoelectric transducers CE are connected to the high-voltage generation units GA1 and GB1 via the signal lines LA1 and LB1, and high frequency electric signals are supplied to the piezoelectric transducers.

Figure 7:
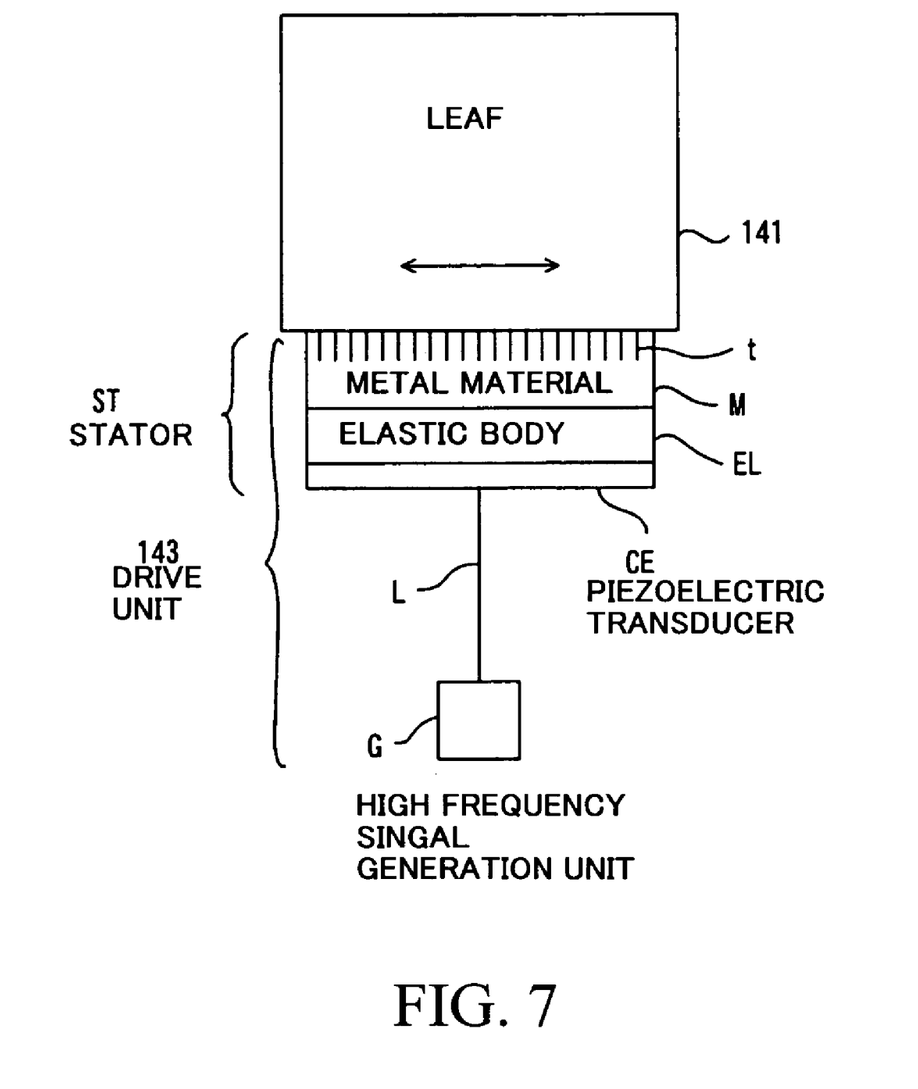
FIG. 7 is an enlarged view of the drive unit in FIG. 6.

With reference to FIG. 7, the leaf 141 and the drive unit 143 are explained. The second drive units and the leaves 141A1 to 141An and 141B1 to 141Bn are the same as or similar to the following drive unit 143 and the leaf 141.

The stator ST which strongly contacts the edge of the leaf 141 with the contact pressure is first explained.

The stator ST, as a single unit, includes a piezoelectric transducer CE, a metal material M and an elastic body EL positioned therebetween, and a surface of the metal material M directly contacts the edge of the leaf 141. Furthermore, a plurality of comb-shaped grooves t are created on a contact side of the metal material to the leaf 141, and the groove extends in a direction perpendicular to a width direction of the leaf 141. Each piezoelectric transducer includes an electrode, and the high frequency electric signal is supplied from the high-voltage generation unit G to the electrode via the signal line L.

Figure 8:
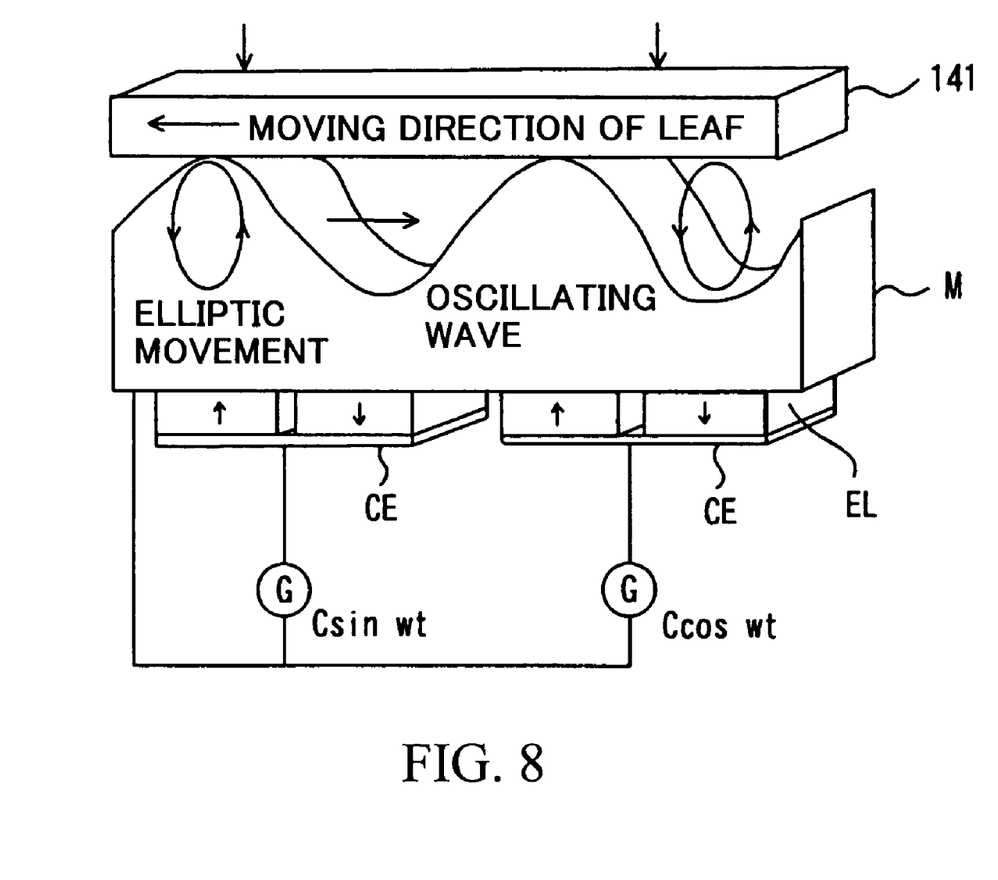
FIG. 8 is an illustration for explaining a principle of an operation of the drive unit.

An operation of the drive unit is explained with reference to FIG. 8. In FIG. 8, the same reference numbers are attached as illustrated in FIG. 7.

When the predetermined high frequency voltage of the high frequency signal is supplied from the high-voltage generation unit G to the piezoelectric transducer CE, an ultrasonic vibration is generated in the piezoelectric transducer CE. This generated ultrasonic vibration proceeds in one direction continuously, bending a metal material M of the stator ST. That is, as if a wave of a sea wimples in one direction, the ultrasonic vibration generated in the piezoelectric transducer CE bends the stator ST.

Therefore, a plane, which contacts the stator ST, of the leaf 141 includes a portion where a head of the wave contacts and another portion where the head does not contact. On the head (peak) of the wave which contacts the plane of the leaf 141, elliptic movement occurs on the contacting point, a track of the elliptic movement is drawn in an opposite direction to a movement direction of the wave proceeding on the stator ST, and a long axis of the elliptic movement is different from the movement direction of the wave. Therefore, in response to influence of the elliptic movement, the leaf 141 moves in an opposite direction to the movement direction of the wave proceeding on the stator ST.

Therefore, when the stator ST is fixed, the leaf 141 is movable and the wave occurs on the stator ST in a right direction, the elliptic movement occurs in a left direction on each peak which contacts the leaf 141. In response to the elliptic movement, the leaf 141 moves in the left direction to the stator ST. On the other hand, when the wave proceeds in the left direction on the stator ST, the leaf 141 moves in the right direction. Thus, by controlling the high frequency signal supplied to the piezoelectric transducer CE of the stator ST, it is possible to move the leaf 141 in an arbitrary direction.

The plurality of comb-shaped grooves t are provided on a side, which contacts the leaf 141, of the metal material M of the stator ST, in order to enlarge amplitude of the elliptic movement and reduce friction The present invention may be not limited to the above embodiments, and various modifications may be made without departing from the spirit or scope of the general inventive concept. For example, although it is explained in the above embodiment that the outside surface of the leaf 141 contacts the stator ST, an inside surface of the leaf 141 may contact the stator ST to move the leaf 141.

As explained above, according to the embodiment, the following various effects, which does not limit the present invention, are considered, for example.

In a first effect, when the leaf is moved directly by the stator which mainly includes the piezoelectric transducer, a driving mechanism can be simplified and miniaturized. Therefore, it is possible to reduce the thickness of each leaf and increase the number of leaves, and the irradiation range of radiation can be approximated to the medical treatment range more.

Figure 9A:
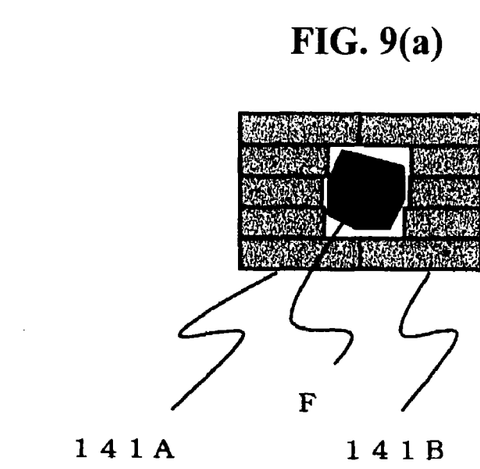
FIG. 9 is an illustration for explaining an operation of the embodiment in comparison with conventional collimator.
Figure 9B:
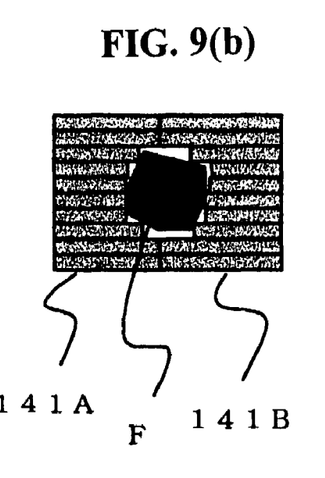

In a case where the collimator 14 is the same size, radiation ranges, about the second groups of leaves 141A and 141B, formed by conventional small number of thick leaves and by large number of thin leaves in the embodiment are illustrated in FIGS. 9A and 9B, respectively. In FIG. 9A showing the conventional small number of thick leaves, large gaps (unnecessary radiation range) occur even when the radiation range is approximated to a shape of diseased part F as much as possible. In FIG. 9B showing the large number of thin leaves in the embodiment, since the radiation range is approximated to the shape of the diseased part F more, the unnecessary radiation range can be reduced.

In a second effect, since a gear mechanism is not used to move the leaves, the backlash does not occur, and an error of a stop position of the leaves can be reduced, and setting accuracy of the radiation range can be improved.

In a third effect, since speed is controllable in stepless, high accurate speed control and position control are possible, and the stop position accuracy of the leaves is improved. Moreover, since operation noise is reduced, it is suitable as a medical apparatus.

In a forth effect, since the leaf and the metal material of the stator are contacted in high contact pressure, even after the supply of the high frequency voltage to the piezoelectric transducer is stopped, namely power supply is stopped, a brake function which maintains holding power continues. Once the position of the leaf fixed, the position is maintained and interference between adjacent leaves is reduced, and therefore the setting accuracy of the radiation range is improved. In addition, the metal material M may be placed on farther positions from the isocentre than a maximum radiation range when the leaves 141A1 and 141A2 are positioned in furthermost positions. In this case, the metal materials do not block the radiation ray.

What is claimed is:

1. A radiotherapy apparatus, comprising:
   a radiation source configured to radiate a radiation ray;
   a multi leaf collimator, including a plurality of leaves, configured to limit a radiation range of the radiation ray; and
   a drive unit configured to move at least one of the leaves with an ultrasonic wave.

2. The radiotherapy apparatus according to claim 1, wherein the drive unit comprises:
   a metal material contacting a contact edge of the leaf in a contact pressure;
   a piezoelectric transducer which is placed on an opposite side to the contact edge of the metal material; and
   a signal generation unit configured to supply an electric signal to the piezoelectric transducer.

3. The radiotherapy apparatus according to claim 2, wherein the signal generation unit comprises:
   a first drive circuit which is provided to each leaf of a first band of leaves among the plurality of leaves; and
   a second drive circuit which is provided to each leaf of a second band of leaves among the plurality of leaves.

4. The radiotherapy apparatus according to claim 3, further comprising:
   a switch circuit, connected to the second drive unit, configured to select at least one leaf to be moved by the second drive unit among the second band of leaves.

5. The radiotherapy apparatus according to claim 4, wherein:
   the first band of leaves are positioned on an inner side to an isocentre; and
   the second band of leaves are positioned on an outer side to the isocentre than the first band of leaves.

6. The radiotherapy apparatus according to claim 2, wherein the piezoelectric transducer is placed on a side edge of the leaf.

7. The radiotherapy apparatus according to claim 2, wherein the piezoelectric transducer and the metal material are placed on farther positions from an isocentre than a maximum radiation range.

8. A radiotherapy apparatus, comprising:
   a radiation source configured to radiate a radiation ray;
   a multi leaf collimator, including a plurality of leaves, configured to limit a radiation range of the radiation ray; and
   means for moving at least one of the leaves with an ultrasonic wave.

9. The radiotherapy apparatus according to claim 8, wherein the means for moving comprises:
   a metal material contacting a contact edge of the leaf in a contact pressure;
   a piezoelectric transducer which is placed on an opposite side to the contact edge of the metal material; and
   a signal generation unit configured to supply an electric signal to the piezoelectric transducer.

10. The radiotherapy apparatus according to claim 9, wherein the signal generation unit comprises:
    a first drive circuit which is provided to each leaf of a first band of leaves among the plurality of leaves; and
    a second drive circuit which is provided to each leaf of a second band of leaves among the plurality of leaves.

11. The radiotherapy apparatus according to claim 10, further comprising:
    a switch circuit, connected to the second drive unit, configured to select at least one leaf to be moved by the second drive unit among the second band of leaves.

12. The radiotherapy apparatus according to claim 11, wherein:
    the first band of leaves are positioned on an inner side to an isocentre; and
    the second band of leaves are positioned on an outer side to the isocentre than the first band of leaves.

13. The radiotherapy apparatus according to claim 9, wherein the piezoelectric transducer is placed on a side edge of the leaf.

14. The radiotherapy apparatus according to claim 9, wherein the piezoelectric transducer and the metal material are placed on farther positions from an isocentre than a maximum radiation range.

15. A method for controlling a radiotherapy apparatus, comprising:
    radiating a radiation ray;
    limiting a radiation range of the radiation ray with a plurality of leaves; and
    moving at least one of the leaves with an ultrasonic wave.

* * * * *